United States Patent [19]

Carr et al.

[11] Patent Number: 4,943,633
[45] Date of Patent: Jul. 24, 1990

[54] CATALYTIC PREPARATION OF CYANOALKYL LACTAMS

[75] Inventors: Richard V. C. Carr, Allentown; Thomas A. Johnson, Orefield, both of Pa.

[73] Assignee: Air Products and Chemicals, Inc., Allentown, Pa.

[21] Appl. No.: 209,733

[22] Filed: Jun. 22, 1988

[51] Int. Cl.$^5$ .................. C07D 201/08; C07D 471/02
[52] U.S. Cl. .................................. 540/531; 540/310; 540/451; 540/476; 540/533; 540/579; 544/282; 546/243; 548/553
[58] Field of Search ............... 540/531, 310, 533, 451, 540/476, 579; 544/282; 546/243; 548/553

[56] References Cited

U.S. PATENT DOCUMENTS 3,761,436  9/1973  Hoshimoto et al. ............ 260/251 A
4,024,172  5/1977  Martel et al. ....................... 549/422
4,794,109  12/1988 Lang .................................. 540/310

FOREIGN PATENT DOCUMENTS 45-41226  12/1970  Japan .
1121924   7/1968   United Kingdom .

OTHER PUBLICATIONS

Benson et al., J. Am. Chem. Society, vol. 70, pp. 2115-2118, 1948.

Primary Examiner—Richard L. Raymond
Assistant Examiner—Ba K. Trinh
Attorney, Agent, or Firm—Russell L. Brewer; James C. Simmons; William F. Marsh

[57] ABSTRACT

This invention relates to an improved process for the preparation of cyanoalkyl lactams by the reaction of an unsaturated nitrile with a lactam, said cyanoalkyl lactam of the formula

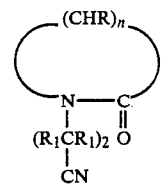

wherein R is H, or methyl, $R_1$ is H, methyl or ethyl and n is a number ranging from 2-11 and wherein each of the methylene groups may carry a lower alkyl substituent as shown. The improvement comprises: reacting said lactam with an alpha-beta unsaturated nitrile having from 3-6 carbon atoms in the presence of a catalytic amount of a diazabicycloalkene of the formula

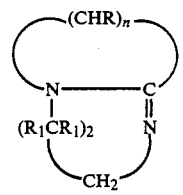

wherein R, $R_1$ and n have the above meaning.

Typically, acrylonitrile is reacted with $\epsilon$-caprolactam in the presence of diazabicycloundecene.

8 Claims, No Drawings

CATALYTIC PREPARATION OF CYANOALKYL LACTAMS

TECHNICAL FIELD

This invention related to the preparation of cyanoalkyl lactams such as cyanoethyl caprolactam by the catalytic hydrogenation of an unsaturated nitrile with a lactam in the presence of a diazabicycloalkene.

BACKGROUND OF THE INVENTION

Diazabicycloalkenes are known and have found use as a catalyst in the preparation of polyurethanes and use in producing various industrial chemicals. For example, ammonia has been reacted with ethylene dichloride in the presence of a diazabicycloalkene to produce ethyleneimine; mononitrobenzene can be reacted with hydrogen in the presence of diazabicycloundecene to form aniline.

Processes for preparing diazabicycloalkenes typically involve three steps, the first comprising the reaction of an unsaturated nitrile with a lactam to produce a cyanoethyl lactam; the second comprising the hydrogenation of the cyanoalkyl lactam in the presence of a hydrogenation catalyst and ammonia to produce an N-(amino-alkyl)-lactam and the third step comprising the cyclic dehydration of the N-(amino-alkyl)-lactam to produce the diazabicycloalkene. The following patents illustrate the preparation of diazabicycloalkenes and particularly 1,8-diazabicyclo[5.4.0]undecene-7 which is commonly referred to as DBU.

U.S. Pat. No. 3,761,436 discloses the preparation of diazabicycloalkenes from N-(amino-alkyl)-lactams and focuses on the third step in the process i.e., the cyclization and dehydration of the N-(amino-alkyl)-lactam to form the diazabicycloalkene. The patentees point out that the reaction conventionally was carried out in the presence of an acid such as phosphoric or hydrochloric acid and noted that addition salts were formed with the bicyclic compounds formed in the dehydration. The resulting acid addition salts which were formed had a tendency to concentrate in the distillation still and resulted in yield loss if not removed. Dehydration and cyclization is accomplished by carrying out the reaction in the presence of an oxide of tin or antimony and a water-immiscible solvent such as toluene or xylene.

Japanese Patent 42-19793 discloses a process for preparing DBU and discusses the three step procedure of cyanoethylating caprolactam followed by reduction and dehydration. The patentees noted that the cyanoethylation of 2-pyrrolidone to produce 1,5-diaza-bicyclo(4.3.0)nonene-5 (DBN) was known and that DBU could be prepared by the cyanoethylation of ε-caprolactam by reacting with acrylonitrile. DBU was preferred to DBN because it was substantially more active in urethane catalysis than DBN. The patentees point out that the cyanoethylation of the lactam should be carried out in the presence of a basic catalyst such as sodium metal, alkali metal, hydroxides, alkali metal salts, alcoholates and amines. Hydrogenation of the cyanoethyl lactam produced is carried out using a hydrogenation catalyst e.g. Raney nickel in an inert solvent such as a lower alkanol. The dehydration and cyclization of the aminopropyl lactam is performed at temperatures below 300° C. in organic solvents such as toluene and xylene and mixed with modest levels of acid e.g., phosphoric or sulfuric acid.

British Patent 1,121,924 discloses a process for producing bicyclic amidines by dehydrating an N-(aminoalkyl)-lactam in the presence of a mineral acid at elevated temperatures.

SUMMARY OF THE INVENTION

This invention relates to improved process for the preparation of cyanoalkyl lactams of the formula by the reaction of an unsaturated nitrile with a lactam, said cyanoalkyl lactam of the formula:

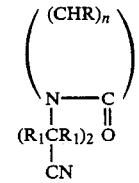

wherein R is H, or methyl, $R_1$, is H, methyl or ethyl and n is a number ranging from 2–11. The improvement resides in carrying out the reaction in the presence of a catalytic amount of a diazabicycloalkene of the formula

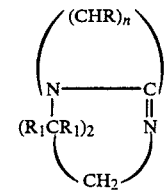

wherein R and n have the above meaning. Typically, acrylonitrile is reacted with ε-caprolactam in the presence of diazabicycloundecene.

There are significant advantages associated with the cyanoalkylation of lactams in the presence of a catalytic amount of a diazabicycloalkenes in view of the fact that the diazabicycloalkene is the ultimate product of the reaction. By utilizing diazabicycloalkenes as a solvent and catalyst, one can one eliminate the use of various bases as catalysts e.g. alkali metal hydroxides which must be removed prior to the hydrogenation reaction. Further, diazabicycloalkenes minimize polymerization of the unsaturated nitrile with itself and the polymerization of the lactam since many of these polymerizations are base catalyzed. In addition, hydrogenation is simplified because the salts formed during neutralization may cause catalyst fouling, and even though water can be added to dissolve the salts, the addition of water presents problems because it must be removed in the third step which effects dehydration and cyclization of the N-aminoalkyllactam to the diazabicycloalkene product.

DETAILED DESCRIPTION OF THE INVENTION

In the first step in the ultimate preparation of diazabicycloalkenes, and particularly 1,8-diaza-bicyclo(5.4.0)undec-7-ene(DBU), an alpha-beta unsaturated nitrile having from 3–6 carbon atoms is reacted with a lactam in presence of a diazabicycloalkene to produce the cyanoalkyl lactam. In this reaction the alpha-beta unsaturated nitrile can be represented by the formula

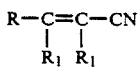

wherein R is hydrogen or methyl and $R_1$ is hydrogen, methyl or ethyl. Representative examples include acrylonitrile, methacrylonitrile, and 1-methyl-2-butenylnitrile.

The addition of the alpha-beta unsaturated nitrile to form the cyanoalkyl lactam is achieved by utilizing lactams of the formula

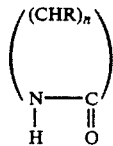

wherein n ranges from 2–11 and R is H or methyl. Examples include β-propiolactam, γ-butyrolactam, δ-valerolactam, ε-caprolactam, ε-methyl-ε-caprolactam, ζ-caprylolactam and ζ-laurylolactam.

This reaction is carried out in the presence of a diazabicycloalkene which is an amidine of the formula

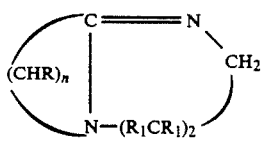

Examples of diazabicycloalkenes include 1,6-diazabicyclo[5.5.0]dodecene-6; 1,7-diazabicyclo[6.5.0]tridecene-7; 1,8-diazabicyclo[7.4.0]tridecene-8; 1,5-diazabicyclo[4.4.0]decene-5; and 1,10-diazabicyclo[7.4.0]tridecene-9.

The diazabicycloalkene of the above formula is utilized both as a solvent and as a catalyst for the reaction. Typically, the concentration of diazabicycloalkene ranges from 20 to 60% of the lactam utilized in the process. When less than 20% said diazabicycloalkene is used, there may be insufficient levels at a solvent.

For purposes of practicing the invention, the reaction is carried out at a temperature of from 50° to 80° C. at pressures ranging from 0 to 20 psig. Temperatures greater than 80° C. tend to form polymerization products and offer no significant advantages in terms of conversion or selectivity. In view of the fact that the ultimate objective of the cyanoalkylation of the lactam is to ultimately produce a diazabicycloalkene, it is preferred that the diazabicycloalkene utilized as the solvent and catalyst for the cyanoalkylation reaction is based upon a lactam and unsaturated nitrile common to the unsaturated nitrile and lactam used in the cyanoalkylation reaction. As is manifest the use of a common diazabicycloalkene minimizes separation difficulties at a later stage even though diazabicycloalkenes of different composition would have sufficient catalytic and solvent activity for effecting the cyanoalkylation of the lactam.

As noted in prior processes the resulting cyanoalkyl lactam then converted to the amine through hydrogenation. Hydrogenation is accomplished via conventional techniques and may be carried out using various solvents such as benzene, xylene and lower alcohols using hydrogenation catalysts such as palladium, platinum, or nickel. Of these Raney nickel is the preferred catalyst for carrying out the catalytic hydrogenation.

One of the advantages of utilizing a diazabicycloalkene in the first step of the synthesis of diazabicycloalkene, i.e., the cyanoakylation of a lactam is that it need not be removed prior to hydrogenation. It may be used as a solvent in the hydrogenation step. Further, the diazabicycloalkene need not be neutralized or removed since it does not adversely affect the performance of the hydrogenation catalyst, e.g., a Raney nickel as a catalyst for the hydrogenation.

After hydrogenation of the cyanoalkyl lactam, ring closure of the N-(aminoalkyl)lactam, is achieved through the dehydration and simultaneous cyclization of the N-(aminoalkyl)lactam chain to form the resultant diazabicycloalkene composition. This reaction, as is known, is acid catalyzed and can be effected by simply adding modest levels of catalyst to the reaction. Example of acids include phosphoric acid, sulfuric acid, toluenesulfonic acid and acid salts. The diazabicycloalkenes form salts with such acids and such salts may be destroyed easily after cyclization.

The dehyration and cyclization reaction is carried out at a temperature from 100° C. to 150° C. at conventional pressures ranging usually from 0.5 to 14.7 psia. In view of the fact that water is generated as a byproduct in the dehydrogenation and cyclization of the N-(aminoalkyl)lactam to the diazabicycloalkene and in view of the fact the reaction is reversible it is important to remove water as quickly as possible from the product in order to avoid yield losses. One technique is to azeotrope the water by carrying out the reaction in the presence of an organic solvent such xylene or toluene and then removing the solvent from the diazabicycloalkene under vacuum distillation. To avoid production of oligomers and other heavy materials the distillation is controlled such that a temperature in excess of 150° C. is avoided.

The following examples are provided to illustrate various embodiments of the invention and are not intended to restrict the scope thereof.

EXAMPLE 1

Preparation of Cyanoethyl Caprolactam in DBU

Approximately 25 grams (0.192 mols) of DBU was placed into a 250 milliliter three-necked round bottom flask. The DBU was heated to 50° C. and then 80 grams (0.71 mols) of molten ε-caprolactam was added to the DBU. The temperature was increased to approximately 63°–67° C. by means of an external water bath and then 40 grams (0.75 mols) of acrylonitrile was added dropwise over a period of about 40 minutes. Reactor contents were stirred while maintaining the 63°–67° C. temperature. After all of the acrylonitrile was added, the solution was cooled to 50°–55° C. with additional stirring for about one hour. At that time it was believed the reaction was concluded. GC analysis indicated that the caprolactam conversion was greater than 96%.

Based on these results it was apparent DBU had sufficient catalytic activity for effecting reaction between acrylonitrile and ε-caprolactam and also sufficient solvent power for acting as a solvent for the reactants.

EXAMPLE 2

Preparation of Aminopropyl Caprolactam in DBU

Approximately 7 grams of Raney nickel 2400 catalyst was charged to a 300 cc autoclave equipped with a mechanical stirrer. Then 15 grams of anhydrous ammonia and 120 grams of the reaction product containing DBU from Example 1 was added to the autoclave. Approximately 16.7% by weight of the reaction mixture consisted of DBU. The temperature of the reaction mass was raised to 90° C. and the pressure raised to 850 psig by introduction of hydrogen. The reactor contents were agitated at this temperature and pressure for 2 hours and 40 minutes at which point hydrogen uptake was 100% of theoretical. After such time it was believed the reaction was complete and the reactor contents were analyzed by GC. The analysis showed a reaction product consisting of 76.1% of N-(ε-aminopropyl)caprolactam and 23.9% DBU. Even though the amount of DBU is greater than the amount in the initial reactor feed, it is believed this is due to some ring closure of the N-(ε-aminopropyl)caprolactam during hydrogenation. This example shows that hydrogenation can take place using DBU as the solvent and thus avoid product separation after cyanoethylation of caprolactam. When alkali metal hydroxides were used, salts formed which must be dissolved in order to avoid catalyst deactivation, etc.

EXAMPLE 3

Comparative Example

Preparation of Cyanoethyl Caprolactam and Attempted Hydrogenation

Approximately 30.9 grams of toluene were charged to a 250 milliliter three-necked round-bottom flask equipped with reflux condenser and pressure-equalizing dropping funnel. The toluene was warmed to 50° C. and then 81 grams (0.716 mols) of molten caprolactam was added followed by 300 microliters of 50 grams of potassium hydroxide. The solution was stirred and then 39.1 grams (0.736 mols) of acrylonitrile were added over a period of 45 minutes while maintaining a temperature at 55°-60° C. with an external water bath. The solution was allowed to stir at 50° C. for an additional two hours. At this point the potassium hydroxide was neutralized by adding 300 microliters of phosphoric acid. The reaction mass was cooled and water (10 milliliters) was added to dissolve the salts. Conversion of caprolactam was 97% as measured by GC.

The resulting caramel-colored solution was then submitted for catalytic hydrogenation without purification as was done in Example 2. As noted from the prior art, and from this example, the cyanoethylation of caprolactam using potassium hydroxide requires neutralization and addition of water to dissolve salts that are formed as a result of the neutralization.

We claim:

1. In a process for the preparation of a diazabicycloalkene of the formula:

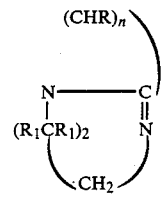

wherein R is H, or methyl, $R_1$ is H, methyl or ethyl, and n is a number ranging from 2-11 by reacting a lactam with an alpha-beta unsaturated nitrile having from 3-6 carbon atoms under conditions for producing a cyanoalkyl-lactam of the formula:

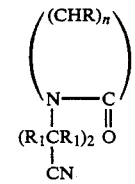

wherein R is H, or methyl, $R_1$ is H, methyl or ethyl, and n is a number ranging from 2-11; and then,
hydrogenating the cyanoalkyl-lactam under conditions for reducing the nitrile group to the amine intermediate N-amino alkyl lactam and effecting dehydration and cyclization of the N-amino alkyl lactam and thereby forming said diazabicycloalkene, the improvement which comprises:
reacting said lactam with said alpha-beta unsaturated nitrile having from 3-6 carbon atoms in the presence of a catalyst consisting essentially of a diazabicycloalkene of the formula:

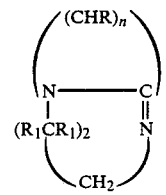

wherein, R, $R_1$, and n have the above meaning; and without effecting separation of the cyanoalkyl-lactam reaction product prior to effecting hydrogenation.

2. The process of claim 1 wherein said diazabicycloalkene is present in a proportion of from 20 to 60% by weight of said lactam.

3. The process of claim 2 wherein n of said diazabicycloalkene is identical to n of said cyanoalkyl-lactam.

4. The process of claim 3 wherein n is 3.

5. The process of claim 4 wherein R is H.

6. The process of claim 1 wherein said lactam is ε-caprolactam and said unsaturated nitrile is acrylonitrile.

7. The process of claim 6 wherein said reacting is carried out at a temperature of from 50° to 80° C.

8. The process of claim 4 wherein $R_1$ is methyl.

* * * * *